(12) United States Patent
Reinprecht

(10) Patent No.: US 8,197,122 B2
(45) Date of Patent: Jun. 12, 2012

(54) DYNAMIC MIXING APPLICATOR

(75) Inventor: Jon Reinprecht, Watertown, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 492 days.

(21) Appl. No.: 12/422,639

(22) Filed: Apr. 13, 2009

(65) Prior Publication Data

US 2009/0268546 A1 Oct. 29, 2009

Related U.S. Application Data

(60) Provisional application No. 61/047,489, filed on Apr. 24, 2008.

(51) Int. Cl.
*A61J 1/00* (2006.01)
*A61M 5/00* (2006.01)

(52) U.S. Cl. .................. 366/279; 366/155.2; 366/156.1

(58) Field of Classification Search ............... 366/110, 366/155.1, 155.2, 156.1, 279; 604/191; 606/214; 222/137, 145.5

See application file for complete search history.

(56) References Cited

U.S. PATENT DOCUMENTS

| | | | |
|---|---|---|---|
| 3,570,719 A | 3/1971 | Schiff | |
| 3,738,773 A | 6/1973 | Tinker | |
| 3,767,085 A | 10/1973 | Cannon et al. | |
| 4,074,363 A | 2/1978 | Croft | |
| 4,198,383 A * | 4/1980 | Konsetov et al. | 422/134 |
| 4,202,635 A | 5/1980 | Hendrickson | |
| 4,432,469 A | 2/1984 | Eble et al. | |
| 4,469,251 A * | 9/1984 | Sperry et al. | 222/135 |
| 4,550,863 A * | 11/1985 | Farrey | 222/145.8 |
| 4,744,521 A * | 5/1988 | Singer et al. | 241/66 |
| 4,934,827 A | 6/1990 | Taschke et al. | |
| 4,986,443 A | 1/1991 | Saur et al. | |
| 5,064,098 A * | 11/1991 | Hutter et al. | 222/137 |
| 5,090,814 A * | 2/1992 | Petcen | 366/162.5 |
| 5,092,492 A * | 3/1992 | Centea | 222/137 |
| 5,184,757 A * | 2/1993 | Giannuzzi | 222/82 |
| 5,271,527 A * | 12/1993 | Haber et al. | 222/43 |
| 5,328,462 A | 7/1994 | Fischer | |
| 5,538,191 A * | 7/1996 | Holl | 241/1 |
| 5,643,206 A | 7/1997 | Fischer | |
| 6,047,861 A | 4/2000 | Vidal et al. | |
| 6,105,822 A * | 8/2000 | Larsen et al. | 222/134 |

(Continued)

FOREIGN PATENT DOCUMENTS

DE 19815550 2/1999

(Continued)

OTHER PUBLICATIONS

European Search Report for EP 09251136.9-1269 date of completion is Aug. 17, 2009 (4 pages).

*Primary Examiner* — Yogendra Gupta
*Assistant Examiner* — Emmanuel S Luk

(57) ABSTRACT

An applicator assembly for mixing, homogenizing and/or emulsifying two or more components is disclosed. The applicator assembly includes a housing configured to receive a motor and a power source, a fluid supply source operably connected to the housing, the fluid supply sources including at least a first and a second source of solution, and a nozzle assembly extending from the housing and in fluid communication with the fluid supply source, the nozzle assembly including a smooth impeller for mixing the at least first and second solutions.

17 Claims, 4 Drawing Sheets

U.S. PATENT DOCUMENTS

| | | |
|---|---|---|
| 6,244,740 B1 | 6/2001 | Wagner et al. |
| 6,309,372 B1 | 10/2001 | Fischer et al. |
| 6,311,871 B1 | 11/2001 | Binder |
| 6,331,172 B1 | 12/2001 | Epstein et al. |
| 6,386,396 B1 | 5/2002 | Strecker |
| 6,443,612 B1 | 9/2002 | Keller |
| 6,506,025 B1 | 1/2003 | Gharib |
| 6,523,992 B1 | 2/2003 | Bublewitz et al. |
| 6,540,395 B2 | 4/2003 | Muhlbauer et al. |
| 6,691,895 B2 | 2/2004 | Strecker |
| 6,834,778 B2 | 12/2004 | Jinbo et al. |
| 6,837,612 B2 | 1/2005 | Bublewitz et al. |
| 6,854,621 B2 | 2/2005 | Keller |
| 6,889,872 B2 | 5/2005 | Herman et al. |
| 6,932,243 B2 | 8/2005 | Keller |
| 6,935,534 B2 | 8/2005 | Strecker |
| 2002/0082563 A1 | 6/2002 | Petersen et al. |
| 2002/0175186 A1 | 11/2002 | Keller |
| 2003/0018298 A1* | 1/2003 | Gellman ............ 604/82 |
| 2003/0090957 A1* | 5/2003 | Kressin et al. ........... 366/139 |
| 2003/0123323 A1 | 7/2003 | Bublewitz et al. |
| 2004/0136846 A1 | 7/2004 | Gharib |
| 2005/0035153 A1* | 2/2005 | Brown ............ 222/145.6 |
| 2007/0191781 A1 | 8/2007 | Richards et al. |
| 2008/0135579 A1* | 6/2008 | Bertram et al. ........... 222/145.5 |
| 2008/0314929 A1* | 12/2008 | Keller ............ 222/145.6 |

FOREIGN PATENT DOCUMENTS

| | | |
|---|---|---|
| DE | 29819661 | 2/1999 |
| EP | 0150738 | 8/1985 |
| EP | 0301201 | 2/1989 |
| EP | 1892033 | 2/2008 |

\* cited by examiner

DYNAMIC MIXING APPLICATOR

CROSS-REFERENCE TO RELATED APPLICATION

The present application claims the benefit of and priority to U.S. Provisional Application Ser. No. 61/047,489, filed on Apr. 24, 2008, the entire content of which is incorporated herein by reference.

BACKGROUND

1. Technical Field

The present disclosure relates to applicators, applicator systems, and the like, for mixing, homogenizing and/or emulsifying two or more solutions and/or substances prior to application, and more particularly, to an applicator system for emulsifying a polyurethane based adhesive/sealant and water prior to application.

2. Background of Related Art

Polymers and other synthetic materials are currently being developed for use in internal and external wound closure. "Bioadhesives" are known in the art, as are various methods for applying the bioadhesive. Bioadhesives offer many significant advantages over conventional wound closure methods, i.e., using sutures, staples, clips or other suitable mechanical fasteners. Bioadhesives are faster and easier to apply, leaving wounds with less scaring, and reducing the need for a follow-up visit to remove any mechanical fasteners.

Most bioadhesives are composed of components that have a tendency to immediately activate and in some instances, rapidly polymerize when combined with one another. Because of this immediate activation and/or rapid polymerization of the bioadhesive, the components comprising the bioadhesive may not be combined until immediately prior to application. An applicator for mixing and applying a polyurethane base adhesive/sealant mixed with water is disclosed in commonly owned U.S. Patent Application Publication No. 2008/0267005, the entire contents of which are hereby incorporated by reference in their entirety. The '005 Application discloses an applicator system including a homogenizing assembly that utilizes rotors and stators to mix, homogenize and/or emulsify two or more solutions. Although effect at emulsifying two or more solutions, a more efficient mixing assembly is desired.

SUMMARY

An applicator assembly for mixing, emulsifying and/or homogenizing two or more solutions is disclosed. The assembly includes a housing configured to receive a motor and a power source, a fluid supply source operably connected to the housing, a nozzle assembly extending from the housing. The fluid supply sources including at least a first and a second source of solution. The nozzle assembly is in fluid communication with the fluid supply source and includes a smooth impeller for mixing the solutions.

In the applicator assembly, the first and second sources of solution may comprise syringes. The housing may further include an actuation assembly for selectively dispensing the solution. The motor is configured to rotate the smooth impeller at about 1,000 to about 35,000 RPM. The nozzle assembly is configured to include an outlet for dispensing said homogenized solution. The housing of the applicator assembly may define a pistol grip or a pencil grip. The nozzle assembly may be integrally formed with or selectively detachable form the housing.

The applicator assembly may further include a trigger mechanism for selectively supplying the first and second solutions. The trigger mechanism may include a trigger pivotably mounted to the housing or instead may include a wheel rotationally mounted to the housing.

BRIEF DESCRIPTION OF THE DRAWINGS

The foregoing summary, as well as the following detailed description will be better understood when read in conjunction with the appended figures. For the purpose of illustrating the present disclosure, a preferred embodiment is shown. It is understood, however, that the present disclosure is not limited to the precise arrangement and instrumentalities shown.

DETAILED DESCRIPTION OF EMBODIMENTS

Figure 1:
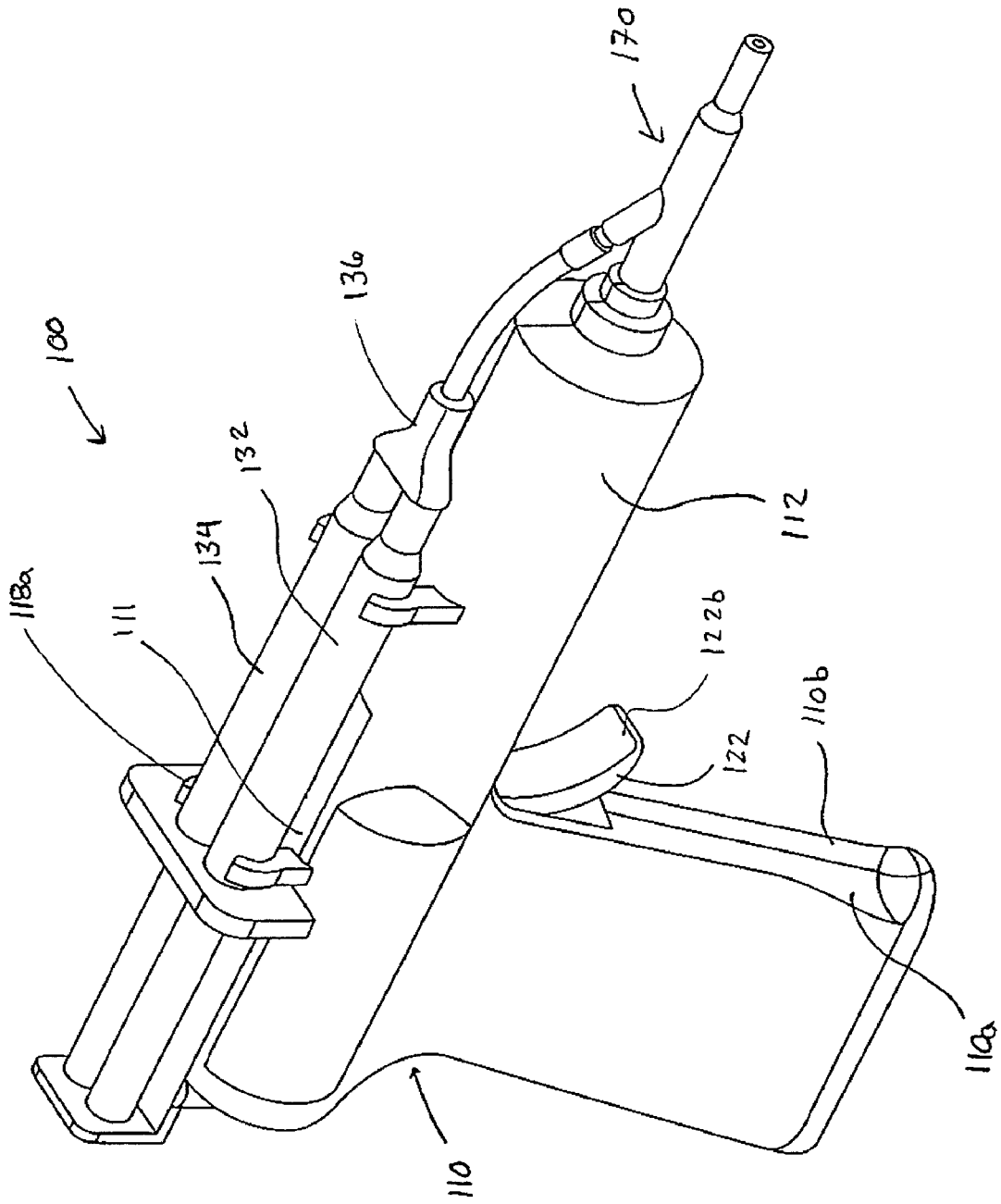
FIG. 1 is a perspective top/side view of the applicator assembly according to an embodiment of the present disclosure.
Figure 2:
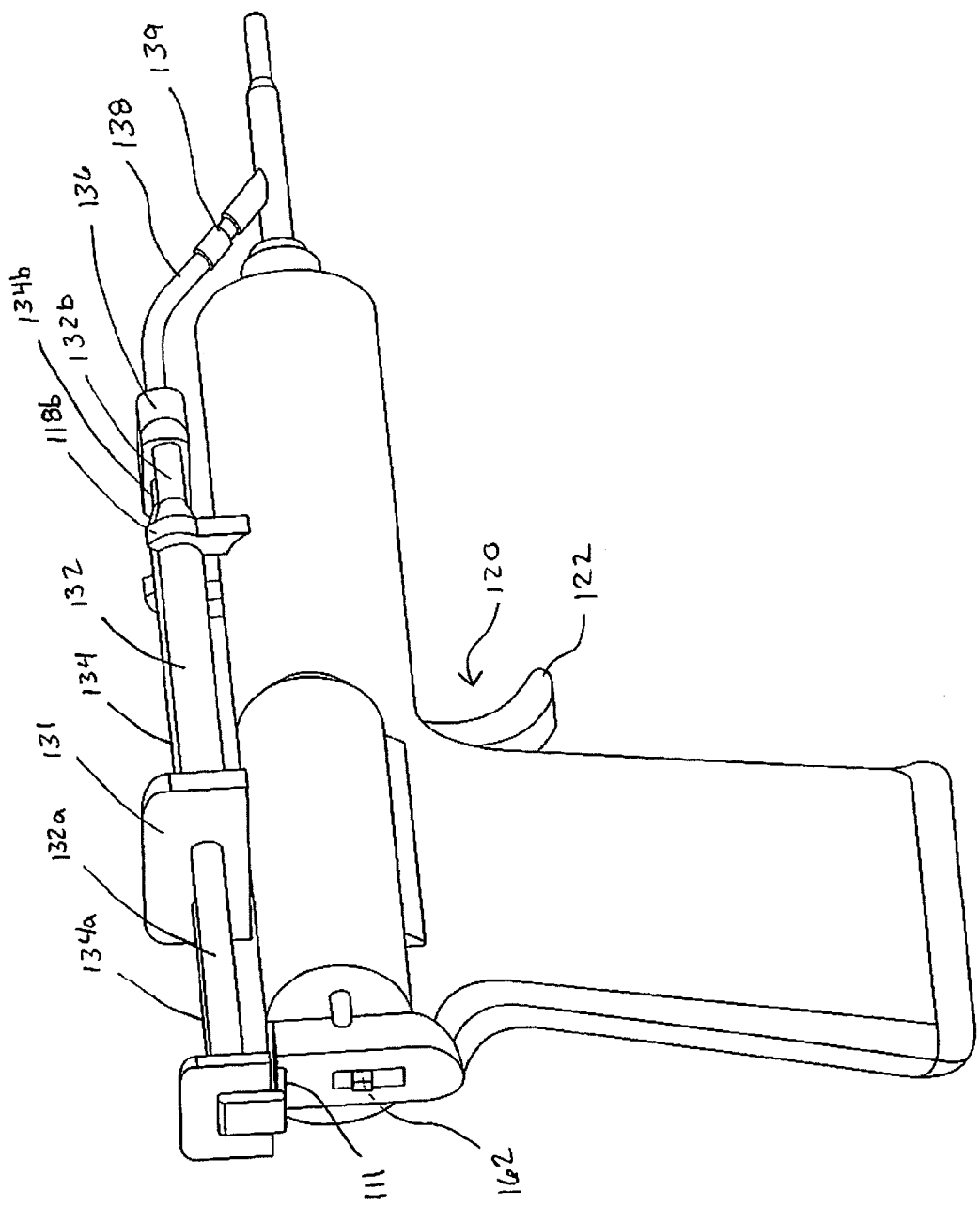
FIG. 2 is a back/side elevational view of the applicator assembly of FIG. 1.

Although the present disclosure relates specifically to the emulsification and/or homogenization of a polymer adhesive and water, aspects of the present disclosure can be incorporated into any apparatus, system or method where two or more solutions require mixing, homogenization, emulsification, or the like, prior to application. Embodiments of the presently disclosed applicator will now be described in detail with reference to the drawings in which like reference numerals designate identical or corresponding elements in each of the several views. As used herein, the term "distal" refers to that portion of the instrument, or component thereof which is further from the user while the term "proximal" refers to that portion which is closer to the user.

Referring initially to FIGS. 1-4, an embodiment of the presently disclosed applicator system is shown generally as applicator assembly 100. Applicator assembly 100 includes a housing 110, a fluid supply source 130 operably engaged with housing 110 and a nozzle assembly 170 extending distally from housing 110.

Figures 3, 4:
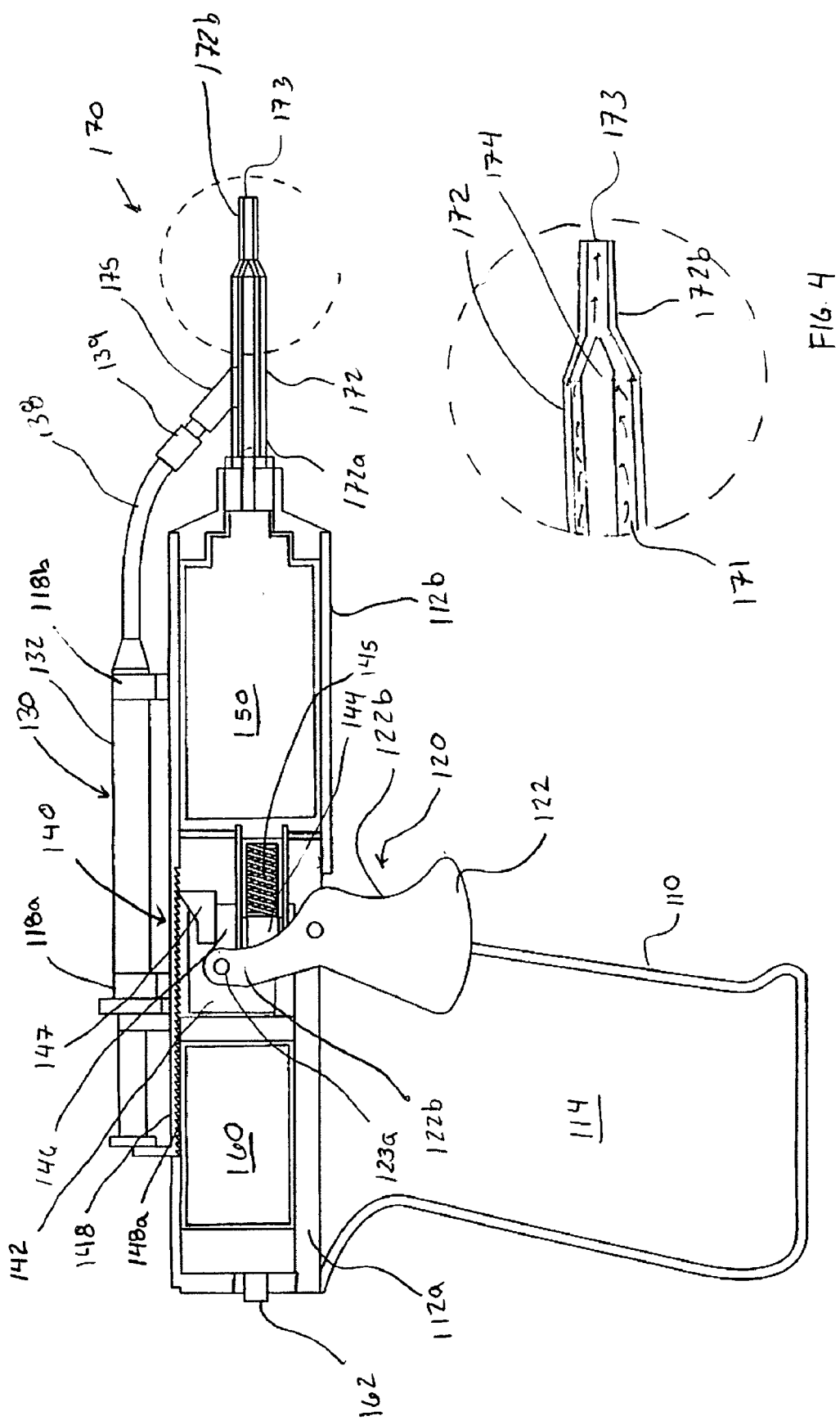
FIG. 3 is a cross-sectional side view of the applicator assembly of FIGS. 1 and 2.
FIG. 4 is an enlarged cross-sectional side view of the distal end of the applicator assembly of FIGS. 1-3.

Housing 110 of applicator assembly 100 includes housing halves 110a, 110b. Housing halves 110a, 110b include a barrel portion 112 and a handle portion 114. As will be discussed in further detail below, barrel portion 112 is configured to retain an actuation mechanism 140 (FIG. 3), a motor 150 (FIG. 3) and a power source 160 (FIG. 3). Barrel portion 112 includes clips 118a, 118b for selectively receiving fluid supply source 130. Handle portion 114 of housing 110 is configured for operable engagement by a user. As will be discussed in further detail below, handle portion 114 includes a trigger mechanism 120 (FIG. 3).

Still referring to FIGS. 1-4, fluid supply source 130 defines a base 131 attached to a first and second syringe or source of fluid 132, 134. Although fluid supply source 130 is shown with two fluid sources, applicator assembly 100 may be configured to dispense more than two fluids. First and second syringes 132, 134 may be of similar or different sizes. Each of first and second syringe, 132, 134 includes a plunger 132a, 134a, respectively, for selectively dispensing fluid from each of first and second syringe 132, 134, respectively. Distal end 132b, 134b of first and second syringes 132, 134, respectively, are in fluid communication with a Y-connector 136. Fluids from first and second syringes 132, 134 initially mix within Y-connector 136. Alternatively, the fluids may be maintained separate as the fluids flow through Y-connector 136. A tube 138 fluidly communicates Y-connector 136 with nozzle assembly 170. As with Y-connector 136, tube 138 may be configured with a single lumen to permit the flow of the mixed fluids or tube 138 may include a plurality of lumen for separately maintaining the fluids from first and second syringes 132, 134. A coupling element 139 is located on a distal end of tube 138 to selectively secure tube 138 with nozzle assembly 170. Coupling element 139 may be threaded, friction fit, include a luer lock or otherwise mechanically attach to nozzle assembly 170.

With particular reference now to FIG. 3, housing 110 is configured to retain trigger assembly 120, actuation mechanism 140, motor 150 and power source 160. Motor 150 may include any motor capable of turning a smooth impeller 174 at speeds of 1-25,000 RPM, and more specifically, at speeds of 1,000 RPM or greater. Motor 150 may be a variable speed motor or may be set for a single speed. Motor 150 is retained within a distal end 112b of barrel portion 112. Power source 160 is located with a proximal end 112a of barrel portion 112. Alternatively, applicator assembly 100 may be configured for operable engagement with a remote power source (not shown). Power source 160 includes a switch or lever 162 for activating motor 150. Power source 160 may further include a knob or second lever (not shown) for adjusting the output of power source 160 and thus, the speed of motor 150.

Still referring to FIG. 3, trigger mechanism 120 includes a trigger 122 pivotally mounted to housing 110 about pivot point 123a. A proximal end 122a of trigger 122 is configured for operable engagement by a user. A distal end 122b of trigger 122 operably engages actuation mechanism 140. Actuation mechanism 140 includes slide member 142. Slide member 142 is slideably positioned within housing 110 and includes a pivot pin 123a for operably engaging distal end 122b of trigger 122. Slide member 142 includes a substantially C-shaped member including first and second extensions 144, 146. First extension 145 engages a spring 145 mounted within housing 110. Second extension 146 includes a pawl member 147 for engaging rack 148. Rack 148 is operably connected to fluid supply source 130 and is configured to slide within groove 111 formed between housing halve sections 110a, 110b. Rack includes notches or teeth 148a along a length thereof for engaging pawl member 147. Rack 148 further includes a flange 149 extending from a distal end 148b for engaging first and second plungers 132a, 134a of fluid supply source 130. As will be discussed in further detail below, as slide member 142 advances longitudinally within barrel portion 114, engagement of pawl member 147 with notches 148a of rack 148 causes rack 148 to also advance. Advancement of rack 148 causes flange 149 to engage plungers 132a, 134a, thereby causing fluid to flow from first and second syringes 132, 134 into Y-connector 136, and then through outlet 175 into nozzle assembly 170.

With reference now to FIGS. 3 and 4, nozzle assembly 170 is operably connected to motor 150 and is fluid communication with fluid supply source 130. Nozzle assembly 170 includes an extension 172 secured to barrel portion 112 of housing 110. Alternatively, extension 172 may be integrally formed with housing 110. Extension 172 defines a passageway 171 along a length thereof for receiving a smooth impeller 174. In an alternative embodiment impeller 174 may including threads or be otherwise configured to assist in mixing of the fluids. A distal end 172b of extension 172 defines an outlet 173 for dispensing a thoroughly mixed fluid, as will be discussed in further detail below. Extension 172 further includes a fluid inlet port 175. Inlet port 175 is configured for operable engagement with coupling element 139.

The operation of applicator assembly 100 will now be described with reference to FIGS. 1-4. Initially, fluid supply source 130 is received within clips 118a, 118b such that first and second plungers 132a, 134b of first and second syringes 132, 134, respectively, are positioned adjacent to flange 149. Tube 138 of fluid supply source 130 is connected to fluid inlet port 175 of extension 172 with coupling element 139. Alternatively, applicator assembly 100 may be provided with fluid supply source 130 previously attached and connected. Once fluid supply source 130 is operably connected to housing 110 and extension 170, motor 150 may be activated using switch 162. Activation of motor 150 causes smooth impeller 174 to rotate within passageway 171 of extension 172.

Once motor 150 is activated, squeezing of trigger 122 causes advancement of slider member 142. Advancement of slide member 142 causes pawl member 144 to engage teeth 148a of rack 148. Advancement of rack 148 causes flange 149 of rack 148 to engage plungers 132a, 132b of first and second syringes 132, 134, respectively. In this manner, the fluids from fluid supply source 130 may be selectively ejected from first and second syringes 132, 134 through tube 138 and into passageway 171 of extension 172. Fluid flowing through passageway 171, is forced between smooth impeller 174 and the inner wall of extension 172. The rotation of smooth impeller 174 causes the mixing, homogenizing and/or emulsifying of the fluids as the fluids flow along the length of extension 172. Nozzle assembly 170 is configured such that the fluids are completely homogenized as the mixture is dispensed through outlet 173. Mixing of the fluids with smooth impeller 174 requires much less force than traditional mixing applicators utilizing rotors and stators. The same is also true of a threaded or grooved impeller.

Figure 5:
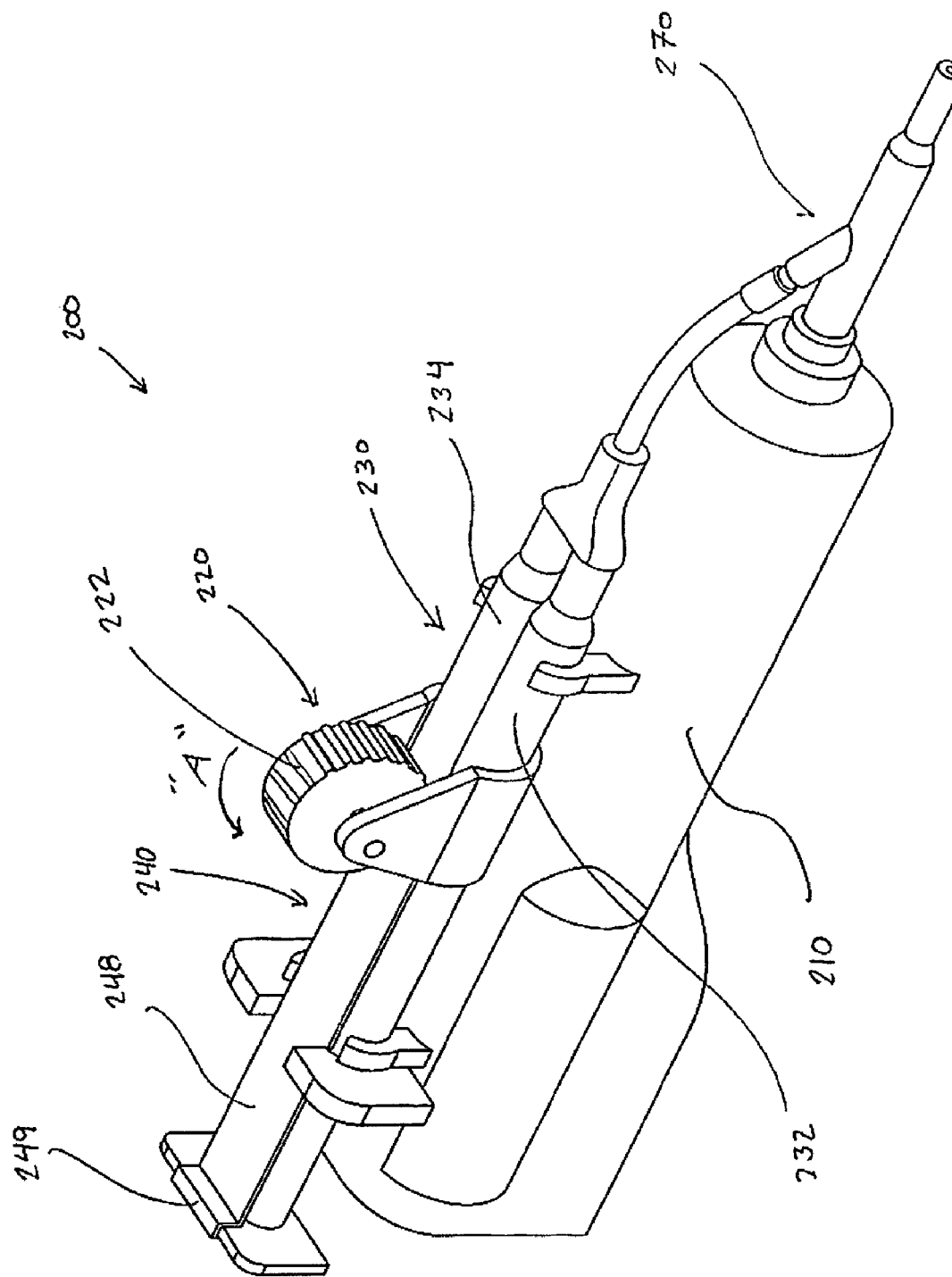
FIG. 5 is a perspective view of an alternative embodiment of an applicator assembly of the present disclosure.

Turning now to FIG. 5, an alternate embodiment of the present disclosure is shown generally as applicator assembly 200. Applicator assembly 200 is substantially similar to applicator assembly 100, and therefore, will only be described as relates to the differences therebetween. Applicator assembly 200 includes a housing 210 defining a trigger mechanism 220, a fluid supply source 230, an actuation mechanism 240, and a nozzle assembly 270.

Still referring to FIG. 5, trigger mechanism 220 includes a trigger or activation wheel 222 operably engaged with a rack 248 of actuation mechanism 240. Rotation of activation wheel 222 in the direction of arrow "A" cause advancement of rack 248. As with applicator assembly 200, advancement of rack 248 causes a flange 249 extending from a distal end of rack 248 to engage first and second syringes 232, 234, respectively. Continued advancement of rack 248 causes fluid to flow from fluid supply source 230 into nozzle assembly 270 where the fluids are mixed as described above.

Thus, it should be understood that various changes in form, detail and operation of the homogenizing applicator system of the present disclosure may be made without departing from the spirit and scope of the present disclosure.

What is claimed is:

1. An applicator assembly comprising:
 a housing configured to receive a motor and a power source;

a fluid supply source operably connected to the housing, the fluid supply source including at least a first and a second source of solution; and a nozzle assembly extending from the housing and in fluid communication with the fluid supply source, the nozzle assembly including a smooth impeller defining a central axis extending the length thereof about which the impeller rotates for mixing the at least first and second solutions.

2. The assembly of claim 1, wherein the at least first and second sources of solution are syringes.

3. The assembly of claim 1, wherein the housing further includes an actuation assembly for dispensing the first and second source of solution.

4. The assembly of claim 1, wherein the motor is configured to rotate the impeller at about 1,000 to about 35,000 RPM.

5. The assembly of claim 1, wherein the motor is configured to rotate the impeller at about 2,500-10,000 RPM.

6. The assembly of claim 1, wherein the nozzle assembly is configured to include an outlet for dispensing a homogenized solution.

7. The assembly of claim 1, wherein the housing defines a pistol grip.

8. The assembly of claim 1, wherein the housing defines a pencil grip.

9. The assembly of claim 1, wherein the fluid supply source is selectively connected to the housing.

10. The assembly of claim 1, wherein the nozzle assembly is integrally formed with the housing.

11. The assembly of claim 1, wherein the nozzle assembly is selectively detachable from the housing.

12. The assembly of claim 1, further including a trigger mechanism for selectively dispensing the solution from the at least first and second sources of solution.

13. The assembly of claim 12, wherein the trigger mechanism includes a trigger pivotably mounted to the housing.

14. The assembly of claim 12, wherein the trigger mechanism includes a wheel rotationally mounted to the housing.

15. An applicator assembly comprising:
a housing configured to receive a motor and a power source, the housing including a handle forming pistol-grip for operable engagement by a user, the housing further configured to selectively receive a fluid supply source including at least a first and a second source of solution;

a nozzle assembly extending from the housing and configured for fluid communication with a fluid supply source, the nozzle assembly including an smooth impeller for mixing at least a first solution and a second solution, wherein the motor is configured to rotate the impeller at about 1,000 RPM to about 35,000 RPM; and an actuation mechanism operatively mounted within the housing for selectively dispensing a first and second solutions from a fluid supply source.

16. An applicator assembly comprising:
a housing configured to receive a motor and a power source, the housing forming a pencil-grip for operable engagement by a user, the housing further configured to selectively receive a fluid supply source including at least a first and a second source of solution;

a nozzle assembly extending from the housing and configured for fluid communication with a fluid supply source, the nozzle assembly including an smooth impeller for mixing at least a first and a second solution; and an actuation mechanism rotatably mounted to the housing for selectively dispensing first and second solutions from a fluid supply source.

17. The applicator of claim 16, wherein the actuation mechanism includes a wheel configured for operative engagement by a user.

\* \* \* \* \*